(12) United States Patent
Werner

(10) Patent No.: US 9,980,768 B2
(45) Date of Patent: May 29, 2018

(54) ELECTROSURGICAL DEVICE WITH IMPROVED INCISION

(75) Inventor: Erich Werner, Wannweil (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 824 days.

(21) Appl. No.: 13/449,421

(22) Filed: Apr. 18, 2012

(65) Prior Publication Data

US 2012/0271304 A1 Oct. 25, 2012

(30) Foreign Application Priority Data

Apr. 21, 2011 (EP) .................................... 11163501

(51) Int. Cl.
*A61B 18/18* (2006.01)
*A61B 18/12* (2006.01)
A61B 18/04 (2006.01)
A61B 18/00 (2006.01)

(52) U.S. Cl.
CPC ........ *A61B 18/1233* (2013.01); *A61B 18/042* (2013.01); *A61B 2018/00601* (2013.01); *A61B 2018/00767* (2013.01); *A61B 2018/00827* (2013.01); *A61B 2018/00857* (2013.01); *A61B 2018/00875* (2013.01); *A61B 2018/1213* (2013.01)

(58) Field of Classification Search
CPC ......... A61B 18/00; A61B 18/04; A61B 18/06; A61B 18/08; A61B 18/12; A61B 18/14; A61B 18/18
See application file for complete search history.

(56) References Cited

U.S. PATENT DOCUMENTS

| 4,473,075 A * | 9/1984 | Rexroth ................. A61B 18/12 606/37 |
| 5,190,517 A | 3/1993 | Zieve et al. |
| 8,257,349 B2 * | 9/2012 | Orszulak ............ A61B 18/1206 606/34 |
| 2007/0282320 A1 * | 12/2007 | Buysse et al. .................. 606/34 |
| 2009/0209956 A1 | 8/2009 | Marion |

FOREIGN PATENT DOCUMENTS

| CN | 1245410 A | 2/2000 |
| CN | 1735383 A | 2/2006 |
| DE | 2504280 | 8/1976 |
| EP | 1 053 720 A1 | 11/2000 |
| EP | 1 849 425 A1 | 10/2007 |
| EP | 1 862 137 A1 | 12/2007 |
| JP | 2506542 B2 | 4/1996 |
| WO | WO 2004/062516 | 7/2004 |
| WO | WO 2009/083617 A1 | 7/2009 |

* cited by examiner

*Primary Examiner* — Michael Carey
*Assistant Examiner* — Elizabeth K So
(74) *Attorney, Agent, or Firm* — Blank Rome LLP

(57) ABSTRACT

To achieve a safe transition from the ignition of a plasma in incision mode to the combustion of the plasma during a cutting mode, an electromedical device to supply an instrument with electrical power is equipped with an ignition recognition mechanism formed by a sensor device. This ignition recognition mechanism switches the HF generator provided in the device from an incision operating mode to a cutting operating mode as soon as ignition is recognized. The switching is brought about by the switching of an HF modulation from a low crest factor in the incision operating mode to a high crest factor in the cutting operating mode.

14 Claims, 2 Drawing Sheets

ELECTROSURGICAL DEVICE WITH IMPROVED INCISION

RELATED APPLICATION

This application claims priority to European patent application EP 11 163 501.7, filed on Apr. 21, 2011, which is hereby incorporated by reference in its entirety.

TECHNICAL FIELD

Embodiments of the invention relate to an electrosurgical device that comprises a device to supply a surgical instrument with electrical power.

BACKGROUND

Electrosurgical devices or systems have been in use for a considerable time. For example, EP 1 053 720 A1 discloses an electrosurgical system, incorporating a surgical instrument and a device, which provides the electrosurgical instrument with HF power. An HF generator, which delivers the corresponding HF voltage, is used for this purpose. The generator is switched on and off in rapid sequence to regulate the power converted at the electrode, where power regulation is possible by setting the duty cycle. This is intended in particular to prevent overheating of the electrode.

To determine the electrode temperature, it is proposed that the voltage at the electrode be investigated for DC components so that a thermionic effect, i.e. a temperature dependent electron emission, can be detected if the electrode becomes too hot. The connected processor establishes this and regulates the duty cycle of the HF voltage to bring about the desired reduction in power. The intention here is to avoid damage to the electrode.

It is further known, for example from US pre-grant publication 2009/0209956 A1, how to monitor the crest factor of the electrode current for an electrosurgical device to draw inferences about whether the electrode is in an incision mode or in a cutting mode. In the incision mode, the electrode is surrounded by water that can conduct ions, e.g., an NaCl solution. It carries a relatively high current. This leads to the development of a vapor bubble at the electrode, in which a plasma discharge can then develop. Once this happens, the crest factor of the flowing current changes significantly. The change occurring in the crest factor is recognized and evaluated for the further control of the device.

It has been found that in particular the transition from the incision to the cutting/ablation phase can be critical. The water enveloping the electrode evaporates very rapidly, so that the power required and actually supplied to the electrode in the incision phase has to be reduced rapidly. If this does not happen, then it is possible for too much power to be supplied in the commencing plasma discharge, leading to undesired effects. On the other hand, it is necessary to work with high power in the incision phase to bring about a reliable development of a vapor bubble and plasma discharge.

SUMMARY

Accordingly, an object of the embodiments of the invention is to provide a mechanism in which an electrosurgical device can switch in a safe and controlled manner from incision mode to cutting mode.

In accordance with the disclosed embodiments, an HF generator is used to provide HF power, the HF generator being connected or connectable to the electrode of an electrosurgical instrument and being controllable in its power delivery. In the simplest case, it can be turned on and off for this purpose.

The HF generator comprises at least one resonant circuit and one amplifier module such as e.g., an electronic switch used as a non-linear amplifier module. This is turned off and on in correct phase to excite the resonant circuit. This periodic switch-on and switch-off of the switch is interrupted in order to interrupt HF power generation. The choice of the duty cycle for the switch-on and switch-off can influence the HF power.

The device in accordance with the embodiments of the invention comprises a sensor device, which recognizes the end of the incision phase and the start of the HF discharge. In this case, it switches the HF generator from the incision mode to the cutting mode. The HF generator is operated with high current delivery in the incision phase while in the cutting mode it operates at lower current.

In the simplest embodiment, the switching between incision and cutting modes is achieved by a change in the crest factor, the HF voltage generated by the HF generator or the generated HF current. The crest factor is the ratio of the peak voltage or current value to the effective value for the voltage or current.

During the incision, the crest factor is preferably between 1.0 and 2.5, and preferably between 1.4 and 2.5, whereas in the cutting/ablation operating mode, a crest factor between 2.5 and 5.0 is used. In a preferred embodiment, the crest factor upon recognition of incipient HP discharge is momentarily switched from the lower value intended for the incision phase to the higher value intended for cutting mode. A sliding control of the crest factor is not implemented at least during this switch-over period, so that transient responses that might lead to undesirable surgical effects are avoided.

Irrespective of the magnitude of the crest factors in the incision and cutting operating modes, it is advantageous if the HF generator generates, in the cutting mode, a crest factor that is greater than the crest factor in the incision operating mode.

The controlled switching of the operating mode of the HF generator from an incision operating mode to a cutting operating mode by switching the crest factor can be achieved by, for example, sudden changing of the duty cycle of a quadratic modulation curve, with which the oscillation delivered by the HF generator is modulated. In other words, to influence the power, the HF generator is switched on and off periodically. In the incision operating mode, there is a high ratio between the switch-on time and the cycle time, whereas in the cutting operating mode there is a lower ratio between switch-on time and cycle time.

In so far as it does not lead to a high input of energy into the biological tissue in the incision mode, a duty cycle of 1 can be used, i.e., a crest factor of 1.4 (sine wave). The HF generator operates here in continuous mode. It is however preferred for a duty cycle of below 1 to be used in incision operating mode too, so that the power introduced into the biological tissue is limited (e.g., 400 Ws/s). It is then possible to use the short blanking intervals of the HF voltage for power reduction. Moreover, upon switching the HF generator on again at the start of each HF oscillation cycle, a higher current pulse is obtained at the electrode, which supports plasma ignition. This is particularly the case if a parallel resonant circuit is used as the HF generator, the coil of which is briefly connected to the full operating voltage at the start of the HF oscillation cycle.

The unit supplying the HF generator (for example, a power pack) can supply a regulated or unregulated operating voltage. The HF generator, however, typically has a (preferably positive) internal resistance, which at low load resistance (i.e., in incision mode) can lead to a reduction in the voltage effective at the electrode.

To allow recognition of the transition from the incision operating mode to cutting operating mode, the current flowing to the electrode or the voltage applied at the electrode can be monitored. If the voltage is monitored, then the commencing incision can be detected on the basis of the increase in voltage at the electrode. While the effective ohmic resistance at the electrode in incision mode is in the region of a few tens of ohms (for example, 25 ohms), in the cutting mode the resistance is markedly higher (for example, greater than 200 ohms).

It is also possible to spectrally examine the current flowing to the electrode or the voltage applied at the electrode to recognize the commencing plasma discharge. A spectral analyzer serving for this purpose can recognize the onset of discharge from the sudden appearance of harmonic waves, which are not present in the incision phase.

It is further possible to use a DC component of the electrode voltage as an indicator for the commencing discharge. This DC component is not based on thermionic effects, but predominantly on field effects and is therefore already seen with a relatively cold electrode. For example, at least with a suitable electrode shape, the field strength-induced electron emission at the electrode can be greater than the electron emission of the tissue, which forms the counter-electrode for the plasma discharge.

BRIEF DESCRIPTION OF THE DRAWINGS

Hereinafter, exemplary embodiments of the invention are explained in greater detail with reference to drawings, in which.

DETAILED DESCRIPTION

Figure 1:
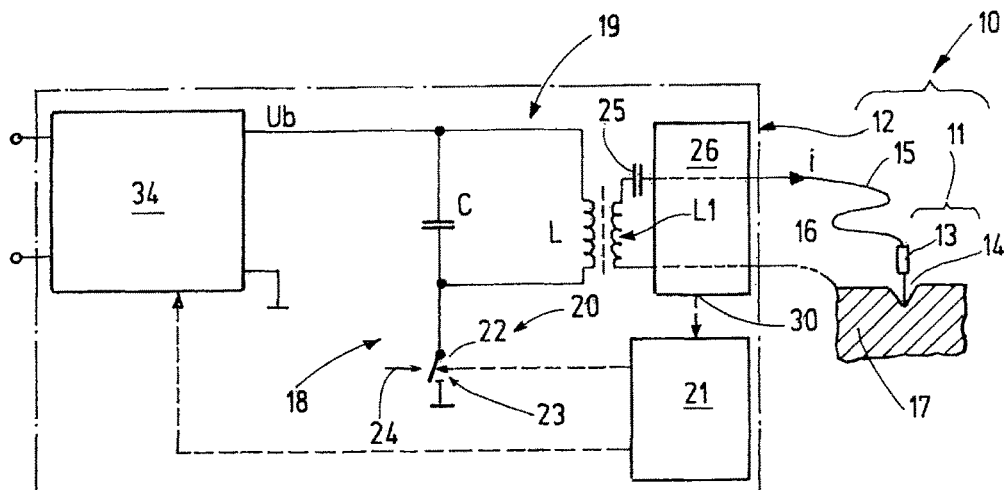
FIG. 1 shows an electrosurgical device in a schematic representation.

FIG. 1 shows an electrosurgical device 10 or an electrosurgical system that has an electrosurgical instrument 11 and an electromedical device 12 for supplying the instrument 11. The instrument 11 is for example, an instrument that can be manipulated by hand by the surgeon with a handle 13, preferably made of an electrically insulating material and an electrode 14, which has an exposed metallic conductor in at least one place; this can have any medically desired shape, for instance spherical, spatula-shaped, blade-shaped, needle-shaped or the like.

Figure 2:
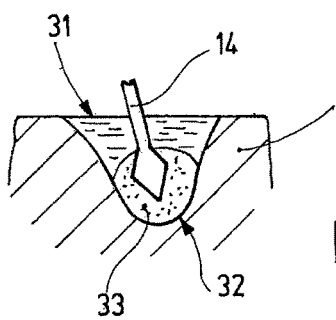
FIG. 2 shows biological tissue with electrode and vapor bubble in a schematic sectional representation.

In the present embodiment, the electrosurgical instrument is, at least in FIGS. 1 and 2, illustrated as a monopolar instrument. It is connected to the device 12 via a feed line 15. In the monopolar embodiment, a further line 16 serving as a return line connects biological tissue 17 (e.g., of a patient on whom the surgical effect is to be brought about) to the device 12. The lines 15, 16 are then housed in separate cables. Line 16 can create a galvanic or capacitive coupling to the tissue 17.

In the representation of FIGS. 1 and 2, the instrument 11 is a monopolar instrument with just one electrode 14. However, it can also be a bipolar instrument, the two electrodes of which are fed by the lines 15, 16. The lines 15, 16 are then preferably housed in a common cable.

The device 12 contains an HF generator 18, which in the present example embodiment is formed by a (parallel) resonant circuit 19, an electronic element 20 for excitation and a control device 21. The electronic element 20 exhibits amplifier characteristics. The element 20 can be of linear or nonlinear design. In the preferred embodiment, it is an electronic switch 22 such as for example, a MOSFET, an IGBT or the like. The electronic switch 22 has a control electrode 23, which is connected to the control device 21 and is provided by the latter with control signals. The switch 22 forms a current path 24, to be opened and closed according to the control signals of the control device 21, between the resonant circuit 19 and the reference potential. The resonant circuit 19 is connected to the operating voltage $U_b$.

The resonant circuit 19 comprises at least one capacitor C and a coil L connected in parallel and preferably providing a resonant circuit of high circuit quality. The resonant frequency of the resonant circuit 19 determines the frequency of the delivered HF voltage of, for example, 350 kHz. While the capacity of the capacitor C is preferably between 50 and 200 nF, the inductance of the coil L is preferably between 4 µH and 1 µH. The coil L couples magnetically with a decoupling coil L1, which is connected via a decoupling capacitor 25 and a sensor device 26 to the lines 15, 16 and thus the electrode 14.

Figure 5:
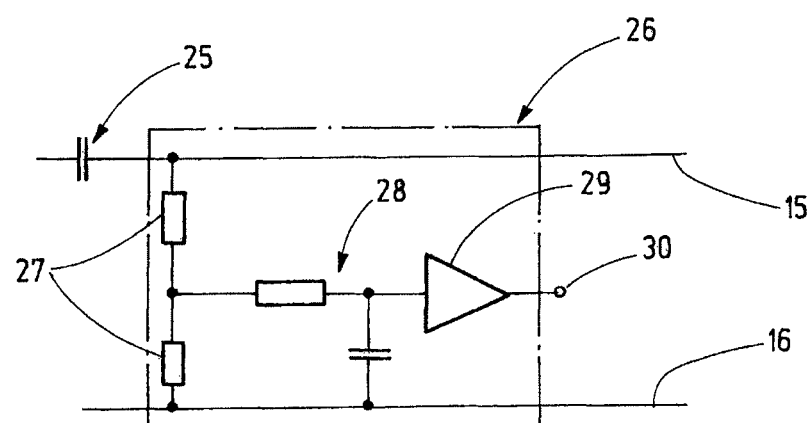
FIGS. 5 and 6 show sensor devices by way of example, in both cases schematically.

The sensor device 26 is used to detect the development of a plasma discharge at the electrode 14. An example sensor device 26 is illustrated in FIG. 5. Its input is a voltage divider 27 connected via the coupling capacitor 25 to the decoupling coil L1. A low-pass filter 28 forms the average voltage value, which is captured by an amplifier 29 and made available at its output 30 as a signal that characterizes the average voltage value. This signal is supplied to the control device 21, which determines whether it is above or below a threshold value and accordingly controls the incision operating mode or cutting/ablation mode. A comparator may also be provided instead of the amplifier 29.

The threshold value of the comparator or control device can be specified such that it is possible to reliably differentiate between a low DC component present during the incision phase and a high DC component of the voltage present at the electrode 14 during the cutting mode. Thus, the signal has a first value during the incision phase and a second value during the cutting phase that differs from the first value. On the basis of these values, the control device 21 detects the operating state of the electrode 14.

Moreover, the device 12 has an operating voltage source, in this embodiment in the form of a controlled power supply 34, which supplies the HF generator 18 and all further components with an operating voltage $U_b$. The operating voltage $U_b$ has a value, for example, of several hundreds of volts, e.g., 400 volts. The operating voltage can be switchable or adjustable for the selection of different surgical effects. In particular it is possible to provide an effect path between the control device 21 and the power supply 34 so that power regulation and/or setting of characteristics of the power supply 34 is possible by components or also operating elements of the control device 21.

The control device 21 can contain one or a plurality of electronic circuits, in particular microcontrollers, which control the operation of the HF generator 18. The function described below of the device 12 in particular allows recognition of the function and thus also the programming of any microcontrollers in the control device 21:

Referring to FIG. 2, a functional description now follows. FIG. 2 illustrates the electrode 14 within the tissue 17 surrounded by a fluid 31. This fluid 31 is, for example, physiological saline solution, possibly mixed with tissue fluid or other fluids. If a surgical effect, for example an incision or the like, is to be effected by the electrode 14, then the HF generator 18 is activated. This can be done using, for example, a switch or other device, not shown here, to be actuated by the surgeon. On this actuation, the HF generator 18 is operated initially in an incision operating mode. The control device 21 brings about rapid closing of the switch 22 and thereafter periodic phased opening and closing to excite the resonant circuit 19 to its resonant frequency. HF power is drawn from the resonant circuit 19 via the decoupling coil L1. A high-frequency current i is thus supplied to the electrode 14. The electrode 14 is in contact with the tissue 17. A high-frequency current i, shown in FIG. 3, flows with an amplitude of several amperes (e.g., 6 to 8 amperes). The resultant relatively high power input brings about sudden evaporation of the fluid present in the vicinity of the electrode and the development of a vapor bubble 32. The transition resistance from the electrode 14 to the tissue 17 suddenly increases in magnitude in the process. An HF gas discharge can form in the steam bubble 32 that develops, generating a plasma 33.

Figure 3:
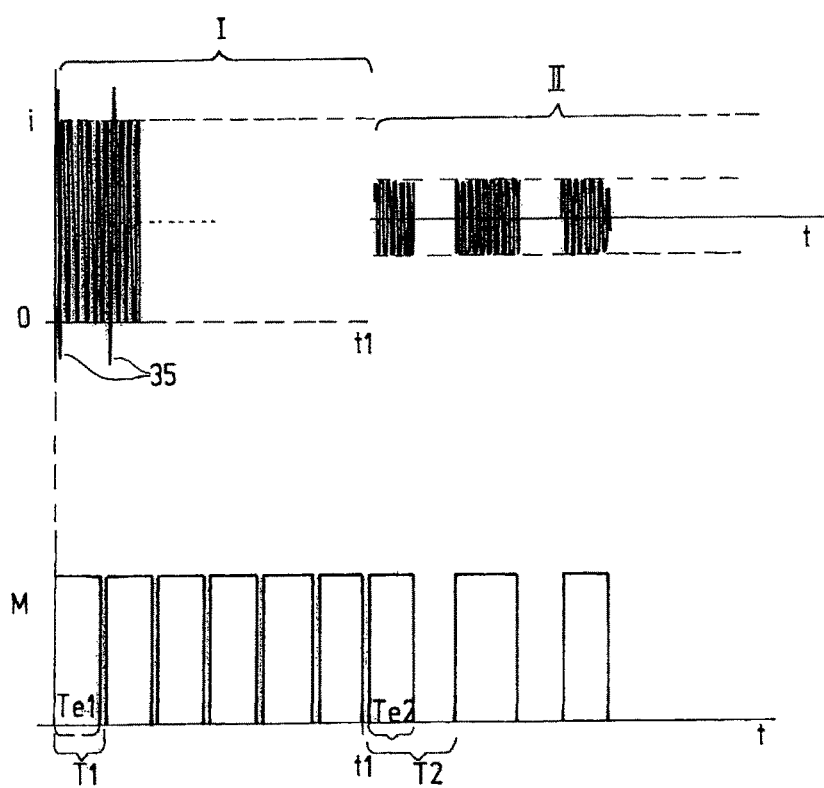
FIG. 3 shows time plots of electrode current, operating voltage and modulation signal.

As a result of the sudden increase in resistance, as can be seen from FIG. 3, at the point in time t1 at which the vapor bubble forms, the flowing current i suddenly becomes lower. The HF AC voltage at the vapor bubble 32 and thus at the lines 15, 16 can immediately develop a DC component due to different electron emissions from the electrode 14 and the tissue 17. This is detected by the sensor device 26. An appropriate signal, appearing at the output 30, reaches the control device 21 and characterizes the transition from incision mode I to cutting mode II.

The signal generated by the sensor device 26 characterizes the transition of the fluid into the gas or vapor phase and thus the development of the vapor bubble 32. This signal is used by the control device 21 to switch the operation of the HF generator 18 from the incision operating mode to the cutting operating mode, which thus applies for points in time greater than t1. This is illustrated in FIG. 3. The value of the current i decreases and the modulation of the high frequency current i starting from a first modulation, which is valid for the period 0 to t1, and thus for the incision operating mode is switched to a second modulation, which is valid for the time after the incision, i.e., for the cutting operating mode.

The first modulation is shown in FIG. 3 on the bottom left. As can be seen, the HF generator 18 operates during incision operating mode with little or no interruptions. Its crest factor is thus approximately 1.4 or slightly above this, but preferably less than at least 2.5. If the HF generator 18 is not working in a continuous mode, but in a pulsed operating mode as indicated on the bottom left in FIG. 3, the duty cycle T1/Te1 is almost 1 and is preferably at least greater than 0.7 to 0.8. T1 is the period of the modulation signal and Te1 is the switching period. This results overall in a crest factor with a value that is slightly greater than 1.4.

At time t1, modulation is switched from the first operating mode into the second operating mode, in which a larger crest factor is present. The duty cycle T2/Te2 is preferably markedly below 0.7. The result is the intermittent HF wave train according to FIG. 3, first upper diagram, right-hand half, for times greater than t1.

The immediate switching from the low crest factor of the incision operating mode to the higher crest factor for the cutting operating mode upon recognition of the development of the vapor bubble 32 prevents the input of excessive power into the forming vapor bubble 32 and thus prevents thermal damage to the tissue 17 and/or to the electrode 14. Moreover, the sudden switching of the modulation (and thus the crest factor) avoids the effects of slow control processes and of transients such as, for example, the rise in the HF voltage after time point t1.

Figure 4:
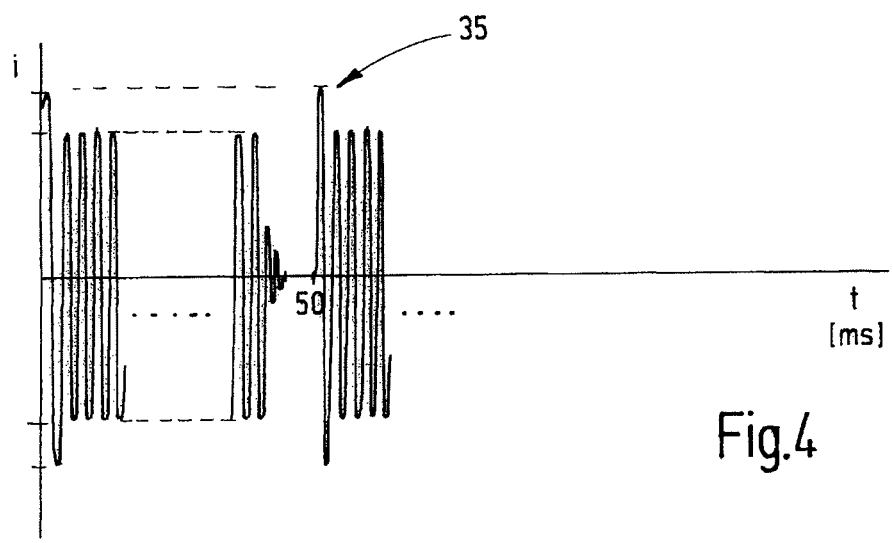
FIG. 4 shows the variation in time of the HF current during the incision phase, over a time interval.

FIG. 4 shows a further aspect that can be used. As is evident, at least with the preferred embodiment, a short periodic blanking of the HF generator 18 is carried out. For example, the duty cycle T1/Te1 has a value of 0.9 and T1 is 50 ms. In the pause lasting approximately 5 ms between two wave trains of the HF voltage of the HF generator 18, the HF voltage settles. For restarting, the switch 22 serving for excitation is closed for a short period. As a result of closing, the switch 22, a first current peak 35 results and can assume large values of, for example, up to 10 $A_{peak}$ and thus leads to a substantial improvement in the ignitability of the plasma 33 in the incision operating mode. This effect can be used independently of the duration of the period T1 and the duty cycle Te1. In this way, an almost continuous HF wave train with periodic current peaks is obtained for the current i during the incision operating mode, caused for example by periodic recurrent transient phenomena of the resonant circuit 19.

All embodiments of the device 10 in accordance with the disclosed principles require reliable recognition of the development of a vapor bubble 32 and the plasma 33. As an alternative to the above-described detection of the DC component of the HF voltage at the electrode 14, other characteristic electrical variables can be evaluated. For example, the HF voltage at the electrode 14 has a lower value during the incision operating mode than during the cutting mode as a result of the internal resistance of the HF generator. The sensor device 26 can be a threshold value circuit. The output signal thereof shows whether the value of the HF voltage is greater than or lower than a suitable specified limit value. The output signal is in turn sent to the control device 21.

Figure 6:
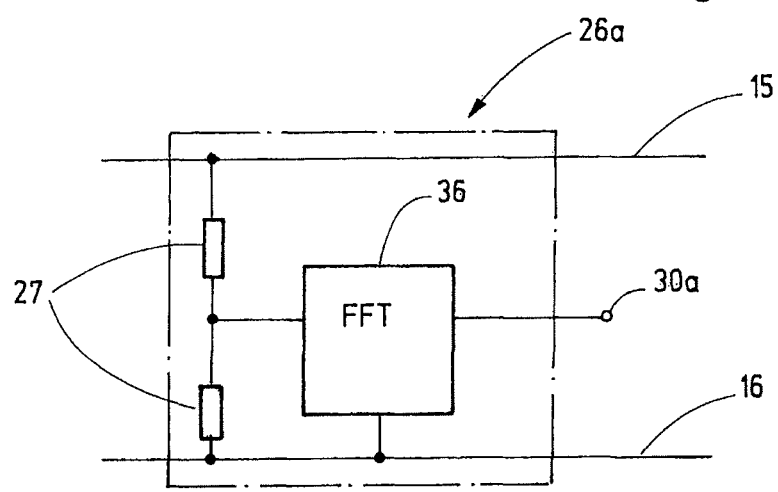

FIG. 6 illustrates a further alternative sensor device 26a. The sensor device 26a has a frequency analysis module 36 connected to the voltage divider 27, which captures the spectrum of the HF voltage between the lines 15, 16. The applied voltage is analyzed by the frequency analysis module 36. This can be carried out by, for example, rapid Fourier transformation (in the illustrated embodiment, carried out by a microcontroller). The frequency analysis module 36 then evaluates the spectrum, for example, for the presence of characteristic spectral lines or spectral components, and sends a signal to the output 30a if the development of the vapor bubble is recognized on the basis of the spectrum. The characteristic change in the spectrum is the result of a change in the characteristics of the transition resistance from the electrode 14 to the tissue 17. As long as the electrode 14 is in contact with the tissue 17 via sodium chloride solution (NaCl) then the transition resistance is approximately linear. As soon as the plasma 33 ignites, it is very substantially non-linear, as a result of which characteristic harmonic waves are generated.

The sensor device 26, 26a is used for immediate initiation of the cutting mode for plasma recognition. If, however, the sensor device 26, 26a recognizes the extinguishing of the plasma 33 due to change in the corresponding signal at the output 33, then the control device 21 can react correspondingly and return the device 12 and its HF generator 18 to the incision operating mode I. It is consequently possible, even with continuously recurring extinguishing events, to work with periodically recurring incision operating mode, for example, to carry out tissue ablations. This applies for all types of the described sensor devices and types of modulation.

To achieve a reliable transition from ignition of a plasma 33 in the incision operating mode to combustion of the plasma 33 during the cutting operation, an electromedical device 12 to supply an instrument 11 with electrical power is equipped with an ignition recognition mechanism formed by the sensor device 26. This ignition recognition mechanism switches the HF generator 18 present in the device 12 from an incision operating mode I to a cutting operating mode II as soon as ignition is recognized. The switching is brought about by the switching of an HF modulation preferably from a low crest factor of less than 2.5 in the incision operating mode to a high crest factor of above 2.5 in the cutting operating mode.

What is claimed is:

1. An electrosurgical device for supplying an instrument with electrical power, said device comprising:
    a controllable high frequency (HF) generator for generating HF power during an initial incision phase of a cutting operating mode in which an electrode placed in a moist tissue milieu evaporates fluid at the electrode and a vapor bubble is generated and during a subsequent cutting phase of the cutting operating mode in which an HF plasma discharge at the electrode is maintained; and
    a sensor device for recognizing an evaporation that has occurred and commencing HF plasma discharge, wherein the sensor device, upon detecting the commencing HF plasma discharge, causes the HF generator to generate a crest factor greater than the crest factor of the initial incision phase, thereby switching the HF generator from the initial incision phase of the cutting operating mode to the cutting phase of the cutting operating mode,
    wherein the HF generator generates, during the initial incision phase, a continuous wave signal, and during the cutting phase, a pulsed HF current generated by switching the HF current on and off, and
    wherein the HF generator generates, during the initial incision phase, a crest factor between 1.4 and 2.5.

2. The electrosurgical device according to claim 1, wherein the HF generator provides the HF power as sine oscillation.

3. The electrosurgical device according to claim 1, wherein the HF generator operates in repeated intermittent mode during the initial incision phase.

4. The electrosurgical device according to claim 3, wherein the HF generator comprises a resonant circuit and an electronic switch connected to the resonant circuit to repeatedly subject the resonant circuit to a full operating voltage.

5. The electrosurgical device according to claim 1, wherein the sensor device has an amplitude detection device.

6. The electrosurgical device according to claim 1, wherein the sensor device has a DC component detection device.

7. The electrosurgical device according to claim 1, wherein the sensor device has a harmonic wave detection device.

8. The electrosurgical device according to claim 1, wherein during operation the HF generator delivers a lower voltage during the initial incision phase than during the cutting phase.

9. A method of operating an electrosurgical device for providing an instrument with electrical power, said device comprising a controllable high frequency (HF) generator and a sensor device, said method comprising:
    controlling the HF generator to generate HF power during an initial incision phase of a cutting operating mode to evaporate fluid at an electrode of a connected surgical instrument and to generate a vapor bubble; and
    controlling the HF generator to generate power during a subsequent cutting phase of the cutting operating mode having an HF plasma discharge at the electrode,
    wherein the sensor device, upon detecting the evaporation and the commencing of the HF plasma discharge, causes the HF generator to generate a crest factor greater than the crest factor of the initial incision phase, thereby switching the HF generator from the initial incision phase of the cutting operating mode to the cutting phase of the cutting operating mode,
    wherein the HF generator generates, during the initial incision phase, a continuous wave signal, and during the cutting phase, a pulsed HF current generated by switched the HF current on and off, and
    wherein the HF generator generates, during the initial incision phase, a crest factor that is between 1.4 and 2.5.

10. The method according to claim 9, wherein the HF power from the HF generator is provided as a sine oscillation.

11. The method according to claim 9, wherein the HF generator is operated in repeated intermittent mode in the initial incision phase.

12. The method according to claim 9, wherein the HF generator has a resonant circuit and an electronic switch connected to the resonant circuit, and the method comprises connecting the resonant circuit repeatedly to a full operating voltage via the electronic switch.

13. The method according to claim 9, wherein an HF amplitude, a DC component and/or a harmonic waves of the HF voltage applied at the electrode are used to recognize a start of HF plasma discharge.

14. The method according to claim 9, wherein the HF generator is operated with a lower voltage during the initial incision phase than during the cutting phase.

* * * * *